United States Patent [19]

Mull

[11] 4,267,723

[45] May 19, 1981

[54] METHOD OF INTRODUCING A LIQUID INTO A MEASURING TUBE

[76] Inventor: John D. Mull, 1905 Fieldgate Dr., Burlington, Ontario, Canada, L7P 3H4

[21] Appl. No.: 58,893

[22] Filed: Jul. 19, 1979

[51] Int. Cl.³ .................. G01N 15/04; G01N 33/48
[52] U.S. Cl. ................................... 73/61.4; 73/425.6
[58] Field of Search ............... 73/61.4, 425.6, 425.4 P

[56] References Cited

U.S. PATENT DOCUMENTS

| | | | |
|---|---|---|---|
| 3,910,103 | 10/1975 | Rose | 73/725.6 X |
| 4,063,460 | 12/1977 | Svensson | 73/425.6 |

FOREIGN PATENT DOCUMENTS

| | | | |
|---|---|---|---|
| 2155239 | 5/1973 | Fed. Rep. of Germany | 73/425.6 |
| 2211098 | 9/1973 | Fed. Rep. of Germany | 73/425.6 |
| 882339 | 3/1943 | France | 73/425.6 |

*Primary Examiner*—Gerald Goldberg
*Assistant Examiner*—Joseph W. Roskos
*Attorney, Agent, or Firm*—Rogers, Bereskin & Parr

[57] ABSTRACT

The disclosure relates to a method of introducing a liquid into a measuring tube and to a device for use in the method. In the specific embodiment the method is used in determining the erythrocyte sedimentation rate of a blood sample. This involves the steps of providing a device comprising a transparent tube and a cap fitted in airtight fashion to a first end portion of the tube and having a skirt which makes airtight sealing engagement with the tube. The cap is slidable along the tube from a first position to a second position closer to the first end of the tube, while still maintaining airtight sealing engagement. A second end portion of the tube is immersed in a blood sample and the cap is slid along the tube towards its said second position to draw a column of blood into the tube. The tube is then removed from the sample and the device is maintained in an upright position for a predetermined length of time. At the end of that time, the extent to which erythrocytes in the blood have settled is determined and provides an indication of the erythrocyte sedimentation rate of the blood sample.

2 Claims, 4 Drawing Figures

METHOD OF INTRODUCING A LIQUID INTO A MEASURING TUBE

This invention relates generally to a method of introducing a liquid into a tube and to a device for use in the method. More particularly the invention has been devised in connection with a method of determining the erythrocyte sedimentation rate of a blood sample.

In the diagnosis of blood disorders, the rate at which erythrocytes (red corpuscles) settle out of a blood sample is commonly used as a primary indicator of whether or not the sample is normal. The sample is placed in a calibrated measuring tube and allowed to stand for a predetermined length of time, after which note is taken of the extent to which the erythrocytes have settled out. In a blood sample containing, say, hepatitis virus, the erythrocytes will settle to a significantly greater extent than in the case of a normal blood sample.

Techniques previously used for introducing a blood sample into a measuring tube have had significant shortcomings. For example, in one case, the blood is aspirated into the tube by mouth; however, this has the risk that the technician performing the technique is exposed to possible contamination by viruses and the like in the blood. Mechanical aspirator devices used to avoid this problem are often difficult to manipulate and do not allow blood to be raised in a steady and controlled fashion, with the result that spillage and contamination of blood samples often occurs.

For example, U.S. Pat. No. 3,373,601 (Monn) discloses a device comprising a container for a blood sample and a calibrated tube which can be inserted into and slid axially of the container. The container has an annular lip which seals against the wall of the tube so that, when the tube is pushed into the container it acts in the manner of a piston, forcing the blood up into the tube. The problem with this device is that, unless extreme care is taken to slowly and carefully push the tube into the container, the tube will be displaced too quickly and the blood will rise rapidly in the tube and squirt out of its open upper end. This is not only highly inconvenient and unhygienic, but is also potentially dangerous since the blood sample may be contaminated.

Broadly considered, an object of the present invention is to provide an improved method of introducing a liquid into a tube. A more particular object is to provide an improved method of determining the erythrocyte sedimentation rate of a blood sample.

According to a first aspect of the invention, there is provided a method of introducing a liquid into a tube. The method involves a first step of providing a device comprising: an elongate transparent tube which is open at both ends and a cap fitted to a first end portion of the tube. The cap has a closed top and a skirt which depends from said top and which makes airtight sealing engagement with the tube. The cap is slidable along the tube from a first position to a second position closer to the first end of the tube than the first position while maintaining said airtight sealing engagement. The next steps are to arrange the cap at its said first position and immerse a second end portion of the tube in a liquid. While maintaining the second end of the tube immersed in the liquid, the cap is then slid along the tube towards its said second position to an extent sufficient to cause liquid to be drawn up the tube to the level of an appropriate one of the graduations. The tube is then removed from the liquid. The lumen of the tube is dimensioned so that the column of liquid is retained in the tube.

According to another aspect of the invention, there is provided a method of determining the erythrocyte sedimentation rate of a blood sample. The method involves a first step of providing a device comprising: an elongate transparent tube which is open at both ends and a cap fitted to a first end portion of the tube. The cap has a closed top and a skirt which depends from said top and which makes airtight sealing engagement with the tube. The cap is slidable along the tube from a first position to a second position closer to the first end of the tube than the first position while maintaining said airtight sealing engagement. The next steps are to arrange the cap at its said first position and immerse a second end portion of the tube in the blood sample. While maintaining the second end of the tube immersed in the blood sample, the cap is then slid along the tube towards its said second position to an extent sufficient to cause blood to be drawn up the tube to an appropriate level. The tube is then removed from the blood sample and maintained in an upright position with the first end portion of the tube uppermost for a predetermined length of time. The lumen of the tube is dimensioned so that the column of blood is retained in the tube. After the predetermined length of time, the extent to which erythrocytes in the blood have settled is determined and provides an indication of the erythrocyte sedimentation rate of the blood sample.

The invention also provides a device for use in performing the method.

In order that the invention may be more clearly understood, reference will now be made to the accompanying drawings which illustrate one embodiment of the invention, by way of example, and in which.

Figure 1:
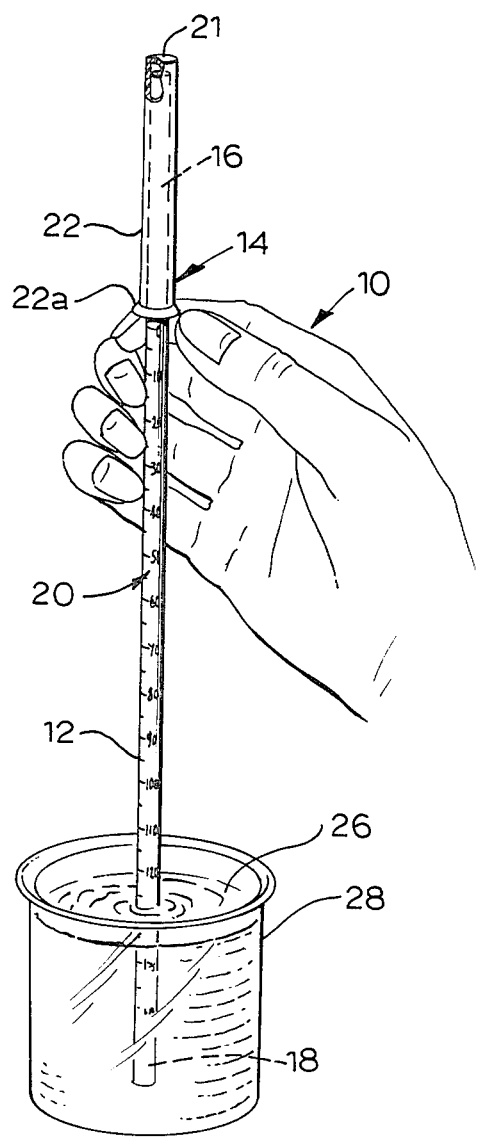
FIG. 1 is a perspective view of the device according to the invention immersed in a blood sample.
Figure 2:
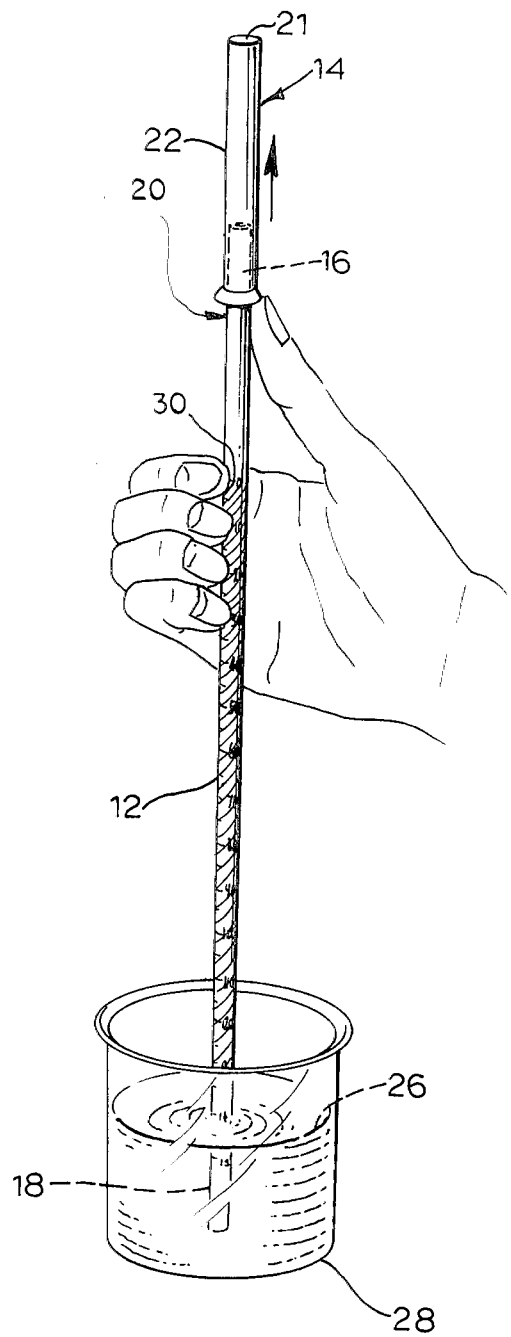
FIG. 2 is a view similar to FIG. 1 and illustrates the manner in which a column of blood is raised in the device.

Referring first to FIGS. 1 and 2, a device for use in determining the erythrocyte sedimentation rate of a blood sample is indicated generally by reference numeral 10. Device 10 includes an elongate transparent tube 12 and a cap 14. Tube 12 is open at first and second ends 16 and 18 respectively and is marked with a series of graduations which extend longitudinally of the tube 12 and which are generally denoted 20. In this embodiment the graduations are in millimeters and tube 12 is made of plastic.

Figure 4:
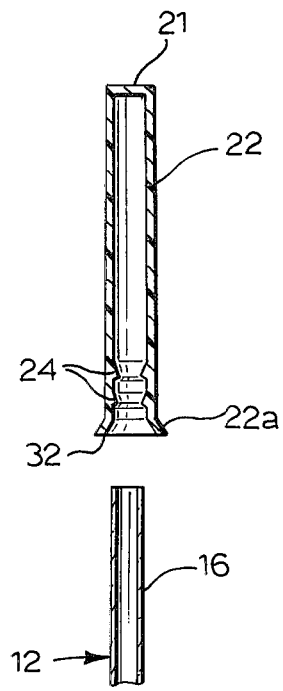

Cap 14 is a one-piece plastic moulding and is fitted in airtight fashion to the first end portion of the tube 12. The cap includes a closed top 21 and a depending generally cylindrical skirt 22 which makes airtight sealing engagement with the external surface of the tube 12. As can best be seen in FIG. 4, skirt 22 is formed with two internal sealing ribs 24 of annular form which engage the external surface of tube 12 and which actually provide the seal between the cap and the tube. Ribs 24 are generally wedge-shaped in cross-section and taper towards top 21 of the cap. The ribs permit cap 14 to be slid longitudinally along the tube 12 while maintaining said airtight sealing engagement. Cap 14 is slidable along the tube from a first position to a second position closer to the first end 16 of tube 12. The cap is shown in typical first and second positions in FIGS. 1 and 2 respectively.

When the device is to be used to determine the erythrocyte sedimentation rate of a blood sample, cap 14 is initially positioned at a suitable first position such as that shown in FIG. 1. The lower (second) end portion of the tube is then immersed in a blood sample as shown in that view. The sample is indicated at 26 and is contained in a laboratory flask denoted 28. While the lower (second) end portion of the tube is maintained immersed in the blood sample, cap 14 is slid along tube 12 towards its upper (first) end. This causes a column of blood to be drawn up into tube 12. Cap 14 is moved along tube 12 to an extent sufficient to draw the column of blood up to the level of an appropriate one of the graduations. In FIG. 2, the blood level is indicated at 30 and is at the level of the "0" graduation 20. However, it will be appreciated that any appropriate graduation may be selected. It will also be realized that the specific locations of the cap 14 in its said "first" and "second" positions are not critical. It is merely necessary that the extent to which the cap is moved be sufficient to draw a column of blood into tube 12 and up to the level of an appropriate one of the graduations.

It will be seen from the drawings that the skirt 22 of cap 14 is outwardly flared in the region of its open end just below the ribs 24 as indicated at 22a, and terminates in a shoulder 32. This shoulder allows a person using the device to grasp the tube 20 between the fingers and palm of one hand and push the cap upwardly on the tube using the thumb of the same hand. This makes for convenient one-handed operation of the device.

Figure 3:
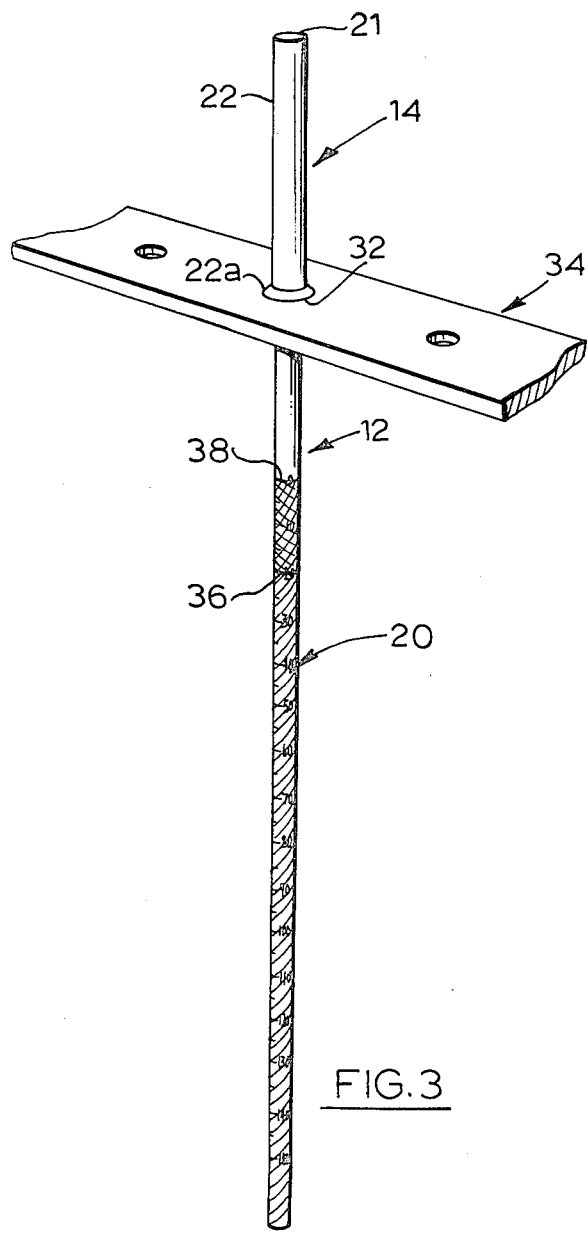
FIG. 3 is a perspective view showing the device supported in a rack during sedimentation of erythrocytes in the blood sample; and, FIG. 4 is an exploded longitudinal sectional view through the device.

After the column of blood has been drawn into the tube 12 of the device as described, the tube is removed from the blood sample and the device is maintained in an upright position with its first end 16 uppermost, for a predetermined length of time. It will of course be appreciated that the lumen of the tube 12 is dimensioned to ensure that the blood is retained in and does not escape from the tube at this time. In FIG. 3, part of a suitable supporting rack for the device is shown at 34. It will be seen that the rack includes a series of openings through one of which the tube 12 is inserted and which is dimensioned so that the device is supported by abutment of the shoulder 32 of cap 14 against the rack.

After the expiry of a predetermined length of time, the extent to which erythrocytes in the blood in tube 12 have settled is determined by reference to the graduations 20. For example, in FIG. 3, the level of the erythrocytes is indicated at 36 and the level of the sample as a whole at 38; the difference in levels is represented by clear blood plasma. Thus, in the present case, it will be seen that the erythrocyte level has dropped by 20 millimeters in the said predetermined length of time. On the basis of this figure, the erythrocyte sedimentation rate of the blood sample can be calculated and a determination made as to whether or not the sample is abnormal.

In some cases, it may be desirable to dilute the blood sample using a sodium citrate solution before determining the sedimentation rate of the sample. The sodium citrate solution acts as an anti coagulent in the sample. Where this is to be done, the device provided by the invention may also be used to introduce the sodium citrate solution into the sample. Thus, by immersing the lower end of the tube of the device in a body of sodium citrate solution in a container and sliding the cap upwardly as described above, a predetermined volume of solution can be drawn into the tube and subsequently discharged into the blood sample by depressing the cap and thereby ejecting the blood sample from the lower end of the tube.

It will of course be appreciated that the preceding description relates to a specific embodiment of the invention and that the invention is not limited to the particular form of the invention described with reference to the drawings. Thus, the invention may be used for introducing any appropriate liquids other than blood samples into measuring tubes and for transferring those liquids to other vessels as required. Examples of detail changes are that, although a plastic tube has been described, the tube could of course be made of glass. The graduations on the tube could be differently arranged and need not be numerically identified. Also, variations in the form of the cap are possible.

I claim:

1. A method of determining the erythrocyte sedimentation rate of a blood sample, comprising the following steps in sequence:

providing a device comprising: an elongate transparent tube which is open at both ends and which is marked with a series of graduations extending longitudinally of the tube; and a cap fitted to a first end portion of the tube and having a closed top and a skirt which depends from said top and makes airtight sealing engagement with the tube, the cap being slidable along the tube from a first position to a second position closer to the first end of the tube than said first position while maintaining said airtight sealing engagement;

arranging the cap at its first said position;

immersing a second end portion of the tube in the blood sample;

while maintaining said second end portion of the tube immersed in the blood sample, sliding the cap along the tube towards its said second position to an extent sufficient to cause blood to be drawn up the tube to an appropriate level determined by reference to said graduations;

removing the tube from the blood sample;

maintaining the tube in an upright position with the first end portion of the tube uppermost for a predetermined length of time; the lumen of the tube being dimensioned so that the column of blood is retained in the tube; and, after said predetermined length of time, determining by reference to said graduations the extent to which erythrocytes in the blood have settled as an indication of the erythrocyte sedimentation rate of the blood sample.

2. A method as claimed in claim 1, wherein the step of sliding the cap along the tube towards its said second position is affected by grasping the tube using the fingers of one hand and sliding the cap upwardly along the tube using the thumb of the same hand.

* * * * *